(12) United States Patent
Zurlo et al.

(10) Patent No.: US 8,293,242 B2
(45) Date of Patent: *Oct. 23, 2012

(54) ULTRA-HIGH YIELD OF ALPHA-1-ANTI-TRYPSIN

(75) Inventors: Gene Zurlo, Kiwah Island, SC (US); Dennis Curtin, Peru, NY (US); Allan Louderback, Temple City, CA (US)

(73) Assignee: Plasma Technologies, LLC, Kiawah Island, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/973,218

(22) Filed: Dec. 20, 2010

(65) Prior Publication Data

US 2011/0152503 A1    Jun. 23, 2011

Related U.S. Application Data

(63) Continuation-in-part of application No. 11/358,431, filed on Feb. 21, 2006, now Pat. No. 7,879,332, which is a continuation-in-part of application No. 11/232,527, filed on Sep. 22, 2005, now Pat. No. 7,879,331, which is a continuation-in-part of application No. 11/217,956, filed on Sep. 1, 2005, now abandoned.

(51) Int. Cl.
*A61K 39/395* (2006.01)

(52) U.S. Cl. .............. 424/177.1; 424/176.1; 424/93.7; 424/520

(58) Field of Classification Search .................. None
See application file for complete search history.

(56) References Cited

U.S. PATENT DOCUMENTS

| | | | |
|---|---|---|---|
| 2,161,861 A | 6/1939 | Gerlough et al. |
| 2,390,074 A | 12/1945 | Cohn |
| 4,067,863 A | 1/1978 | Watt |
| 4,093,606 A | 6/1978 | Coval |
| 4,126,605 A | 11/1978 | Schneider et al. |
| 4,136,094 A | 1/1979 | Condie |
| 4,154,819 A | 5/1979 | Stephan |
| 4,165,370 A | 8/1979 | Coval |
| 4,246,085 A | 1/1981 | Mattock |
| 4,296,027 A | 10/1981 | Condie |
| 4,312,949 A | 1/1982 | Ahrens |
| 4,318,902 A | 3/1982 | Stephan |
| 4,321,192 A | 3/1982 | Jain |
| 4,322,403 A | 3/1982 | Bunnig |
| 4,347,138 A | 8/1982 | Ohno et al. |
| 4,371,520 A | 2/1983 | Uemura et al. |
| 4,404,132 A | 9/1983 | Mitra |
| 4,476,109 A | 10/1984 | Kimura et al. |
| 4,486,282 A | 12/1984 | Bier |
| 4,624,780 A | 11/1986 | Chang |
| 4,639,513 A | 1/1987 | Hou et al. |
| 4,675,384 A | 6/1987 | Dromard et al. |
| 4,692,331 A | 9/1987 | Uemura et al. |
| 4,835,257 A | 5/1989 | Friedrich-Fiechtl et al. |
| 4,877,866 A | 10/1989 | Rudnick et al. |
| 5,177,194 A | 1/1993 | Sarno et al. |
| 5,310,877 A | 5/1994 | Spencer |
| 5,561,115 A | 10/1996 | Tenold |
| 5,886,154 A | 3/1999 | Lebing et al. |
| 6,093,324 A | 7/2000 | Bertolini et al. |
| 6,281,336 B1 | 8/2001 | Laursen et al. |
| 6,307,028 B1 | 10/2001 | Lebing et al. |
| 6,402,913 B1 | 6/2002 | Gilbert et al. |
| 6,485,932 B1 | 11/2002 | McIntosh et al. |
| 6,541,518 B2 | 4/2003 | Shanbrom |
| 6,835,379 B2 | 12/2004 | Andersson et al. |
| 6,875,848 B2 | 4/2005 | Ristol Debart et al. |
| 6,881,573 B2 | 4/2005 | Louderback |
| 6,893,639 B2 | 5/2005 | Levy et al. |
| 7,297,716 B2 | 11/2007 | Shanbrom |
| 2001/0051708 A1 | 12/2001 | Laursen et al. |
| 2002/0151688 A1 | 10/2002 | Ristol Debart et al. |
| 2003/0022149 A1 | 1/2003 | Shanbrom |
| 2003/0036638 A1 | 2/2003 | Joergensen et al. |
| 2003/0129167 A1 | 7/2003 | Shanbrom |
| 2005/0020816 A1 | 1/2005 | Joergensen et al. |

FOREIGN PATENT DOCUMENTS

| | | |
|---|---|---|
| EP | 0440483 | 8/1991 |
| WO | 2006064373 | 6/2006 |

OTHER PUBLICATIONS

Dam, J., et al, "Plasma fractionation based on chromatography and precipitation by polyethylene glycol and caprylic acid", Downstream, Amersham Pharmacia Biotech, vol. 31, pp. 17-18, Mar. 1999.

Li, L., et al, "Purification and Properties of Rat Prothrombin", The Journal of Biological Chemistry, vol. 242, No. 23, pp. 5611-5616, May 15, 1967.

*Primary Examiner* — Yunsoo Kim
(74) *Attorney, Agent, or Firm* — Fish & Associates, PC

(57) ABSTRACT

The instant invention provides novel and effective methods of isolating alpha-1-antitrypsin from cryo-poor plasma and formulating it into therapeutic products. This invention achieves higher yields and a superior quality of alpha-1-antitrypsin. Alpha-1-antitrypsin is isolated from cryo-poor plasma, using one or more salts selected from a group comprising sodium citrate, sodium acetate, sodium gluconate, ammonium sulfate, sodium chloride, sodium sulfate and ammonium chloride in two fractionation steps, followed by diafiltration to remove those salts employed.

14 Claims, 4 Drawing Sheets

ULTRA-HIGH YIELD OF ALPHA-1-ANTI-TRYPSIN

This application for patent is a Continuation-in-Part of U.S. patent application Ser. No. 11/358,431 filed Feb. 21, 2006, which is a Continuation-in-Part of U.S. patent application Ser. No. 11/232,527, filed Sep. 22, 2005, which is a Continuation-in-part of U.S. patent application Ser. No. 11/217,956 filed Sep. 1, 2005.

FIELD OF THE INVENTION

This invention relates generally to methods for separation of components from blood plasma, and, more particularly, to methods for alcohol-free separation of components from blood plasma or other blood based material.

BACKGROUND

Commonly, contemporary methods for separation of components from blood plasma or other blood based material, including IgG, Albumin and Alpha-1-trypsion depend upon early work by Edwin J. Cohn. As found in U.S. Pat. No. 5,177,194 issued Jan. 5, 1993 to Maria E. Sarno, et al. (SARNO), "One scheme in widespread use is the well-known Cohn fractionation method, which is based on differential precipitation using cold ethanol." Cohn et al. J. Am. Chern. Soc. 68, 459 (1946).

A U.S. Pat. No. 2,390,074 issued Dec. 4, 1945 to Edwin J. Cohn (Cohn) disclosed use of alcohol, acetone and dioxane as precipitants in such fractionation processes. Continued dependence upon alcohol as a precipitant is further demonstrated in U.S. Pat. No. 6,893,639 B2 issued May 17, 2005 to Joshua Levy, et al. (Levy), wherein it is stated, "The conventional industrial methods of immune globulins purification from blood plasma are based on cold ethanol fractionation which co-precipitate groups of proteins based on their isoelectric points at given alcohol concentration at sub-zero temperatures."

Cohn's work was stimulated by the need of the military for a stable solution for use as a plasma volume expander during World War II to replace lyophilized plasma. Consequently, the Cohn method focused on optimizing the process for separating the albumin fraction which provides the osmolality necessary for plasma volume expansion.

Even so, the use of alcohol precipitants is not without difficulties, as illustrated by Cohn, "Some protein precipitants, such as alcohol, have a tendency to denature many proteins with which they come in contact, the danger of denaturation increasing with concentration of the alcohol and increase in temperature. For many proteins, it has been found advisable to exercise considerable care in mixing the precipitant with the plasma or other protein solution in order to avoid denaturation of the protein." It is known in the art that alcohol is a denaturant of gamma globulins, but alcohol it is greater a denaturant of alpha-1-trypsin, and for this reason, it is considered prudent to provide an alcohol-free method fractionating alpha-1-trypsin.

Further considerations of combining ethanol and water may be warranted relative to denaturation of proteins. For example, if one adds 500 ml of ethanol (100%) to 500 ml of water, one does not obtain 1000 ml of 50% ethanol. Rather, the final volume is approximately 956 ml. It is surmised that the reduction in volume is due to a tight binding between the ethanol and water molecules. Such binding may be a cause of changes in protein configuration resulting in some permanent denaturation of protein molecules which remains after ethanol is removed and water is returned.

In the 1970's, chromatography was found to be useful in the separation and purification of plasma proteins. Chromatography separates plasma proteins by specifically targeting unique characteristics of each, including molecular size (gel filtration), charge (ion exchange chromatography), and known interactions with specific molecules (affinity chromatography).

The use of various chromatographic methods on an industrial scale has been adopted for the isolation of small-weight, high-value proteins, such as Factor VIII, from plasma, and for the final purification of gamma globulin after separation from the plasma by Cohn, or modified Cohn methodologies. However, chromatographic separation of the large-weight, lower-value fractions such as albumin and gamma globulin, on an industrial scale has not been found to be practical.

Two U.S. patent applications, filed by Edward Shanbrom, having Application Numbers 20030022149 (Shanbrom '149) and 20030129167 (Shanbrom '167) filed Jan. 30, 2003 and Jul. 10, 2003, respectively, teach of use of carboxylic salts (e.g., trisodium citrate) as an agent for enhancing formation of a cryoprecipitate from plasma. The method(s) of Shanbrom generally involve trisodium citrate and other citrate salts as agents for enhancing production of blood clotting factors from cryoprecipitate.

Shanbrom '149 teaches in paragraph 0009 that "It is an object of the present invention to provide enhanced yields of cryoprecipitate." Shanbrom also teaches, in paragraph 0011, that carboxylic acids are effective agents for enhancing the production of blood clotting factors from the cryoprecipitate. Shanbrom '149 notes that the addition of citrate to plasma, especially at concentrations between two and ten percent, by weight, does not appreciably denature labile proteins. Moreover, it is noted in Shanbrom '149 that citrate potentiates or enhances the killing of microorganisms by heat treatment.

Shanbrom '167 notes in paragraph 0015 that, "Not only does added citrate increase the amount of cryoprecipitate, it simplifies the process by decreasing the requirement for freezing . . . " plasma in order to harvest cryoprecipitate. Shanbrom clearly teaches use of production of a cryoprecipitate for the purpose of fractionating products from the cryoprecipitate through the use of trisodium citrate in concentrations of two to ten percent.

In the 1950's, it was discovered that a "cryoprecipitate" derived from blood-based material, contained various factors was useful in treating clotting disorders such as hemophilia. Such a cryoprecipitate, as the name implies, was obtained by freezing blood plasma followed by controlled thawing at zero to four degrees Centigrade to form a liquid suspension of the precipitate. A cryo-poor supernatant derived from the cryo-precipitation process was then available for fractionation using methods according to Cohn to produce albumin and gamma globulin. Subsequent developments led to fractionation of cryoprecipitate into pure concentrates of Factor VIII, von Willebrand Factor, and other clotting factors.

While Shanbrom '149 and '167 deal directly with extracting labile coagulation products from a cryoprecipitate formed through use of citrate compounds, particularly trisodium citrate, and with killing microorganisms in the cryoprecipitate using the citrate compounds, the instant invention deals directly with extracting non-labile products (e.g., albumin, gamma globulin and alpha-1-antitrypsin) from cryo-poor plasma through use of salt compounds. Shanbrom fails to teach a cryo-poor plasma in any way.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

SUMMARY OF THE INVENTION

In brief summary, the instant invention provides novel and effective methods of isolating alpha-1-antitrypsin from cryo-poor plasma and formulating it into therapeutic products. Accordingly, this invention achieves higher yields of a superior quality of alpha-1-antitrypsin by directly and expeditiously separating the alpha-1-antitrypsin from the plasma by means of a non-denaturing precipitant, which may be selectively chosen from a group of organic salts including sodium citrate, sodium acetate, and sodium gluconate and from a group of inorganic salts including ammonium sulfate, sodium chloride, sodium sulfate and ammonium chloride. Two surprising characteristics of use of these salts are that (1) fractionation depends upon employing an effective weight percentage solution and (2) that these salts are effective in such fractionation when used alone and when used in a combined mixture of two or more salts wherein the combination has the same effective weight percentage.

Also, addition of these salts to protein in solution proves to be not as reactive to removal of water as addition of ethanol by previous methods. A rapid isolation using these salts, removal of the resulting fraction followed by removal of salt from the resulting fraction and a quick restoration of the internal water molecule of the protein has proved superior to ethanol fractionation using currently employed methods.

The inventive process is for fractionating blood-based products to produce a useful, nondenatured alpha-1-antyprsin product which involves the following steps:
(a) providing a cryo-poor plasma, physically separated from a cryoprecipitate;
(b) salting the cryo-poor plasma to produce a first intermediate having a total salt content of between 11-13% wt;
(c) centrifuging the first intermediate to produce a first supernatant and a first paste;
(d) salting the first supernatant to produce a second intermediate with a total salt content of between at least 21-23% wt;
(e) centrifuging the second intermediate to produce a second supernatant and a second paste;
(f) rehydrating the first paste, and de-salting the first paste and the second supernatant, and passing the de-salted first paste and the second supernatant through at least one of an ion exchange column or an affinity column to produce first and second alpha-1-antitrypsin effluents; and
(g) combining the first and second effluents to produce a product containing the alpha-1-antitrypsin.

In step (b), the first fractionation utilizes an added concentrated salt solution or addition of dry salt to the cryo-poor plasma to yield an eleven to thirteen percent solution by weight when mixed into a quantity of the cryo-poor plasma. At this concentration, the added salt selectively dehydrates portions of the cryo-poor plasma to form a supernatant and a precipitated residual paste. Note that the supernatant and paste have a resulting salt concentration in the range of eleven to thirteen percent concentration by weight of the selected salt or combination of salts. Preferably the concentration should approximate twelve percent. In step (c) separation of the supernatant and the paste may be accomplished by centrifugation or existing methods which are well known in art. The supernatant is retained for further processing according to the steps of claimed method. The residual paste is processed to recover alpha-1-antitrypsin, but other blood components from the first paste can be recovered such as fibrinogen and albumin from the residual paste. As discussed below in step (f), it is contemplated that the first paste is re-hydrated in water and then de-salted by diafiltration to remove the added salt, and then ran through an ion exchange column or an affinity column to produce a first alpha-1-antitrypsin effluent.

In step (d), the second fractionation utilizes addition of more concentrated salt solution or addition of a sufficient amount of dry salt to the retained supernatant to selectively dehydrate portions thereof to yield a second paste product and a residual second supernatant product. The total concentration by weight of both the second paste and second supernatant should be in a range of approximately twenty-one to twenty-three percent. It is preferred that concentration by weight of the selected salt or combination of salts should approximate twenty-two percent. In step (e), the second paste and the second supernatant may be separated by centrifugation, filtering or other methods which are well-known in the art. The second supernatant is further processed to recover alpha-1-antitrypsin, but other components such as albumin and other proteins may be recovered. In step (f), it is contemplated that the second supernatant is de-salted by diafiltration to remove the added salt, and then ran through an ion exchange column or an affinity column to produce a second alpha-1-antitrypsin effluent. In step (g), the 1st and 2nd alpha-1-antitrypsin effluents are then combined and formulated into the alpha-1-antitrypsin product. Likewise, the albumin recovered from the $1^{st}$ and $2^{nd}$ fractionations can be combined to produce a final albumin product.

Surprisingly, precipitation using salts does not appear to be dependent upon some sort of molar reaction. Rather, precipitation appears to be based upon a simple percentage by weight relationship in both steps (b) and (d). In the following table (Table 1), effective concentrations of both organic and inorganic salts are found. Note the effective concentration by weight is the substantially the same percentage for each salt listed.

TABLE I

Examples of effective concentration of salts which may be used in Steps (a) and (b). Also, surprisingly, the above listed salts may be used in any combination if the total concentration by weight is maintained as cited for steps (a) and (b).

|  | Molecular Weight | Molar Weight in a 12% Solution (for step (a)) | Molar Weight in a 22% Solution (for step (b)) |
|---|---|---|---|
| Organic Salts |  |  |  |
| Sodium citrate | 294 | 0.408M | 0.748M |
| Sodium acetate | 82 | 1.46M | 2.68M |
| Sodium gluconate | 218 | 0.427M | 0.783M |
| Inorganic Salts |  |  |  |
| Ammonium sulfate | 132 | 0.908M | 1.66M |
| Sodium chloride | 58.5 | 2.05M | 3.76M |
| Sodium sulfate | 142 | 0.845M | 1.54M |
| Ammonium chloride | 53.5 | 2.24M | 4.11M | surprisingly, the above listed salts may be used in any combination if the total concentration by weight is maintained as cited for steps (b) and (d).

In step (f), it is preferred to re-hydrate the first paste with water having approximately four times the weight of the paste product, although other volumes of water may be judiciously selected within the scope of the invention.

In step (f) a diafiltration system with a 30 KD filtering membrane may be used to separate the selected salt or salts from the resulting first paste (and excess water in the first paste) and the second supernatant to produce first and second alpha-1-antitrypsin effluents and to permit further processing on an industrial scale. Note, that such filtering is made facile and possible by extracting euglobulins. As used herein, euglobulins are defined to be those globulins which are insoluble in water, but are soluble in saline solutions. Most importantly, if euglobulins are not removed from a solution and if the ionic strength of that solution is lowered towards deionized water (e.g., in the case of the instant invention), euglobulins foul a diafiltration system, thereby rendering it unusable.

The process, according to the instant invention, enables the separation of alpha-1-antityrpsin without exposing it to the denaturing effects of ethanol used in the Cohn process, hence leaving the alpha-1-antitrypsin in a native state. The denaturing effects of alcohol include the formation of polymers, aggregates and the destruction of the alpha-1-antitrypsin molecule. In the absence of the denaturing effects of ethanol, the stabilization of the plasma with the selected salts, results in higher alpha-1-antitrypsin yields.

In summary, the process of the instant invention employs high concentrations of one or more preselected salts combined with subsequent removal of those salts from the alpha-1-antitypsin concentrate by means of diafiltration, a technique which became practical on an industrial scale in the 1980's. Final purification of the resulting alpha-1-antitrypsin is then practically and effectively achieved through the use of well-established chromatographic purification techniques, such by an ion exchange column or an affinity column. The invention reduces production costs as a result of higher yields, fewer fractionation steps, shorter overall processing time, lower energy costs, and lower chemical costs. Capital costs are less because of reduced space requirements, reduced work-in-process, reduced processing time, and elimination of the explosion-proof environments required for ethanol processing.

Various objects, features, aspects and advantages of the inventive subject matter will become more apparent from the following detailed description of preferred embodiments, along with the accompanying drawing figures in which like numerals represent like components.

DETAILED DESCRIPTION

Reference is now made to flow path elements illustrated in FIGS. 1-4. Generally, each rectangular box is used to illustrate a procedural step; each diamond is used to demonstrate a separation step; each oval designates a product resulting from a preceding procedural or separation step; and each circle is used to identify either a starting point or a continuation path.

Figure 1:
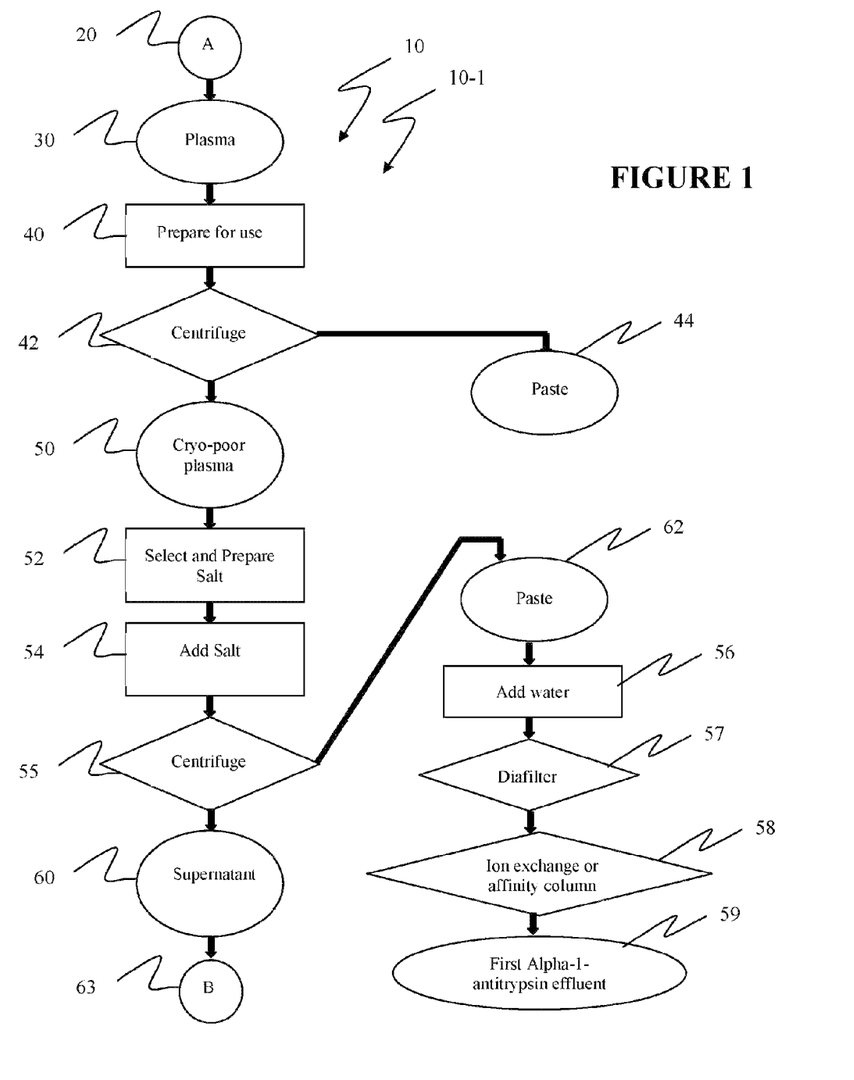
FIG. 1 is a flow diagram of a set of initial steps associated with the method according to the instant invention.

Reference is now made to FIG. 1 wherein an initial portion 10-1 of a preferred alpha-1-antitrypsin process flow path, generally numbered 10, is seen. As indicated after initial starting point 20, a volume of plasma 30 to be processed is selected. In preparation step 40, plasma 30 is frozen and then warmed to approximately five degrees Centigrade to form a cryoprecipiate. While five degrees is the target process temperature, which should be maintained throughout the following steps in process 10, a temperature range between limits of two to eight degrees may be held within the scope of the instant invention. A separation step 42 is used to separate a cryoprecipitate 44 from cryo-poor plasma 50.

A quantity of a salt or salts (which may be selected from salts listed in Table I, provided supra) is selected and prepared for addition to cryo-poor plasma 50 per procedure 52. Due to the fact that a single salt or a combination of salts may be selected and used, it is prudent to consider an added salt quantity as "at least one salt," as a quantity used may contain a single salt or a combination of salts in each of steps (b) and (d), recited supra. Generally, a salt or combination of salts maybe prepared in solution, added as dry salt or added as a combination of hydrated and dry salts. In any event, it is most important to bring the total concentration of added salts to a predetermined concentration by weight.

As an example, when sodium citrate is selected and used, a fifty percent sodium citrate solution is prepared by stirring five hundred grams of sodium citrate into six hundred milliliters of purified water. Stirring time should be thirty to sixty minutes or, alternately, until the sodium citrate is dissolved. At this point, dilute the mixture with pure water to one thousand milliliters. Add 50% citric acid solution to the mixture until a pH of 7.0 is reached.

As is well known in organic chemistry art, the following steps can be used to produce a fifty percent citric acid solution. Add 50 gm of citric acid to 60 ml of purified water. Stirring time should be about 30 minutes or until the citric acid is in solution. After the citric acid is in solution, add enough purified water to bring the volume to 100 ml and mix well. A portion of this solution, added to the 1000 ml of sodium citrate, adjusts the pH to 7.0. Therefore, add the citric acid to the sodium citrate solution until the pH of 7.0 is reached. It should be noted that a very little citric acid needs to be added to adjust to a pH of 7.0.

Preparatory to performing the first fractionation step (step 54), a volume of fractionation solution to be added to cryo-poor plasma 50 is calculated. It is a goal that the salt concentration (in this case sodium citrate fractionation solution) should be twelve percent by weight. Also the pH of the fractionation solution should be approximately 7.0.

The formula, (Formula I) for calculating respective volumes of fractionation solution (sodium citrate) and cryo-poor plasma 50 are as follows:

$$x=(C*V)/(0.5-C)$$

where: x is desired volume of 50% sodium citrate solution; C is a desired fractional concentration by weight of sodium citrate; (e.g., 0.12 or twelve percent): and V is volume of solution to be diluted, (e.g., volume of plasma 50).

An example of a calculation by Formula I is:

For a volume ($V_p$) of plasma 50 of 500 liters, and the desired fractional concentration by weight of sodium citrate is twelve percent:

$$x=(0.12*500)/(0.5-0.12)=158 \text{ liters}$$

Solving Formula I for C yields Formula II into which values of volumes of plasma 50 and sodium citrate may be inserted as follows:

$$C=(0.500*158)/(500+158)=0.12$$

For step 54, over a period of approximately five minutes, the prepared sodium citrate fractionation solution (which may be at room temperature, i.e. approximately twenty degrees Centigrade) is added to cryo-poor plasma 50. Gently stir while adding the sodium citrate solution. Once the sodium citrate solution is completely added to cryo-poor plasma 50, continue gently stirring the resulting slurry for approximately sixty minutes while reducing the slurry temperature to within a range of two to eight degrees Centigrade. (The slurry should maintain pH at approximately 7.0 to 7.1.)

Upon completion of fractionation step 54, centrifuge as procedure 55. It is recommended that a flow-through centrifuge (e.g., a Westphalia Centrifuge) be used to separate component parts of the slurry into a supernatant liquid 60 and a paste 62 by normal procedures for those skilled in the art, while maintaining temperature of the slurry in the range of two to eight degrees Centigrade.

Supernatant liquid 60, contains virtually all of the IgG of the original plasma, and is retained for further processing as an integral part of the instant method. Paste 62 is also processed to recover alpha-1-antitrypsin, but other blood components from the first paste can be recovered such as albumin and blood factors, including Factors VIII, IX, von Willebrand and fibrinogen. It is contemplated that paste 62 is re-hydrated in water at step 56, de-salted by diafiltration at step 57 to remove the added salt, and then ran through an ion exchange column or an affinity column, at step 58, to produce a first alpha-1-antitrypsin effluent 59.

Figure 2:
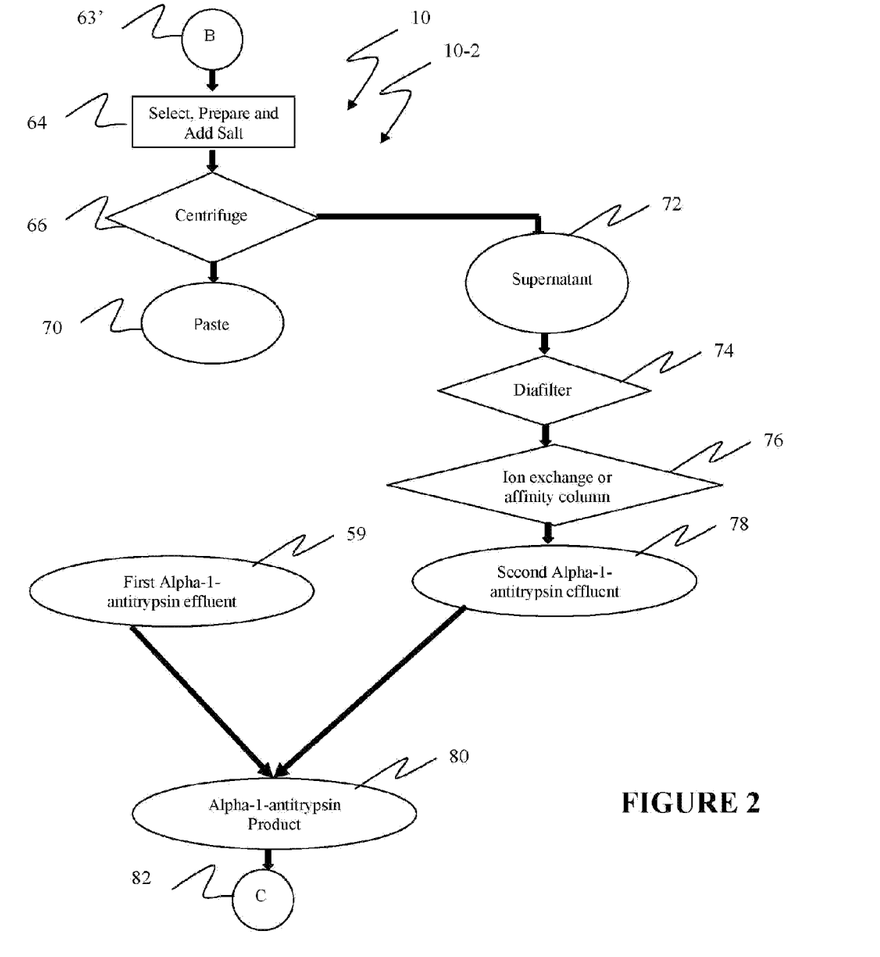
FIG. 2 is a flow diagram disclosing a series of steps which immediately follow the steps seen in FIG. 1.

Reference is now made to FIG. 2 as point 63' for flow path portion 10-2 continues from point 63 of FIG. 1. For the second fractionation phase 64 using sodium citrate, perform process step 64 which adds additional sodium citrate fractionation solution to supernatant 60. Enough fifty percent sodium citrate is added to supernatant 60 to increase concentration by weight of sodium citrate from twelve percent to twenty-two percent. Note that, for other salt or salts used in step 64, the total concentration by weight of the at least one salt used should be in a range of twenty-one to twenty-three percent, preferably in the range of twenty-two percent.

To calculate the volume of fifty percent sodium citrate to be added, Formula III is provided as follows:

$$C_e=((V_{60}*C_{60})+(V_x*C_{0.50}))/(V_{60}+V_x)$$

Where $C_e$ is the desired end concentration by weight of sodium citrate; $V_{60}$ is the volume of supernatant liquid 60; $C_{60}$ is sodium citrate concentration in supernatant liquid 60; $V_x$ is volume of fifty percent sodium citrate to be added; and $C_{0.50}$ is concentration of fifty percent sodium citrate (i.e. 0.50).

Note that the desired end concentration by weight of sodium citrate in solution is 0.22 or twenty-two percent.

Solving for Vx yields Formula IV which may be used to calculate volume of sodium citrate to be added:

$$V_x=V_{60}*(C_e-C_{60})/(C_{0.50}-C_e)$$

As an example, for a volume of $V_{60}$ of 552 liters; a concentration by weight of $C_e$ of 0.22; a concentration by weight of 0.12 for $C_{60}$; and a concentration by weight of 0.50 for $C_{0.50}$:

$$V_x=197 \text{ liters}$$

After adding volume $V_x$ of sodium citrate, stir for two to four hours (though one to two hours is often sufficient for smaller volumes) while retaining the temperature of this mixture between two and eight degrees Centigrade. Note that this solution will change color to a pale yellow as the additional sodium citrate is added and the mixture is stirred.

After stirring, per step 66, centrifuge the mixture, use a continuous flow centrifuge while maintaining the temperature in the range of two to eight degrees Centigrade to separate paste 70 from supernatant 72. The resultant supernatant 72 contains essentially no IgG. Virtually all of the IgG of cryo-poor plasma 50 is now found in paste 70. Supernatant 72 is further processed to recover alpha-1-antitrypsin, but other blood components such as albumin and other proteins may be recovered from supernatant 72. In step 74, it is contemplated that supernatant 72 is de-salted by diafiltration to remove the added salt, and then in step 76 ran through an ion exchange column or an affinity column to produce a second alpha-1-antitrypsin effluent 78. The first alpha-1-antitrypsin effluent 59 and the second alpha-1-antitrypsin effluent 78 are combined and formulated into the alpha-1-antitrypsin product 80.

Contents of paste 70 includes IgG, other serum proteins and sodium citrate. The sodium citrate (and/or other used salt or salts) must be removed from paste 70 to permit IgG to be isolated by ion exchange chromatography. First, paste 70 is liquefied using purified water (of about four times the volume of paste 70), which produces an IgG rich solution. Then removal of sodium citrate (and/or other used salt or salts) is accomplished by continuous diafiltration using purified water. A Millipore (or comparable) diafiltration system equipped with 30 KD cut-off membranes may be employed. Completion of this is indicated when the conductivity of the IgG rich solution is reduced to 100-900 microSiemens/centimeter (μS/cm).

Figure 3:
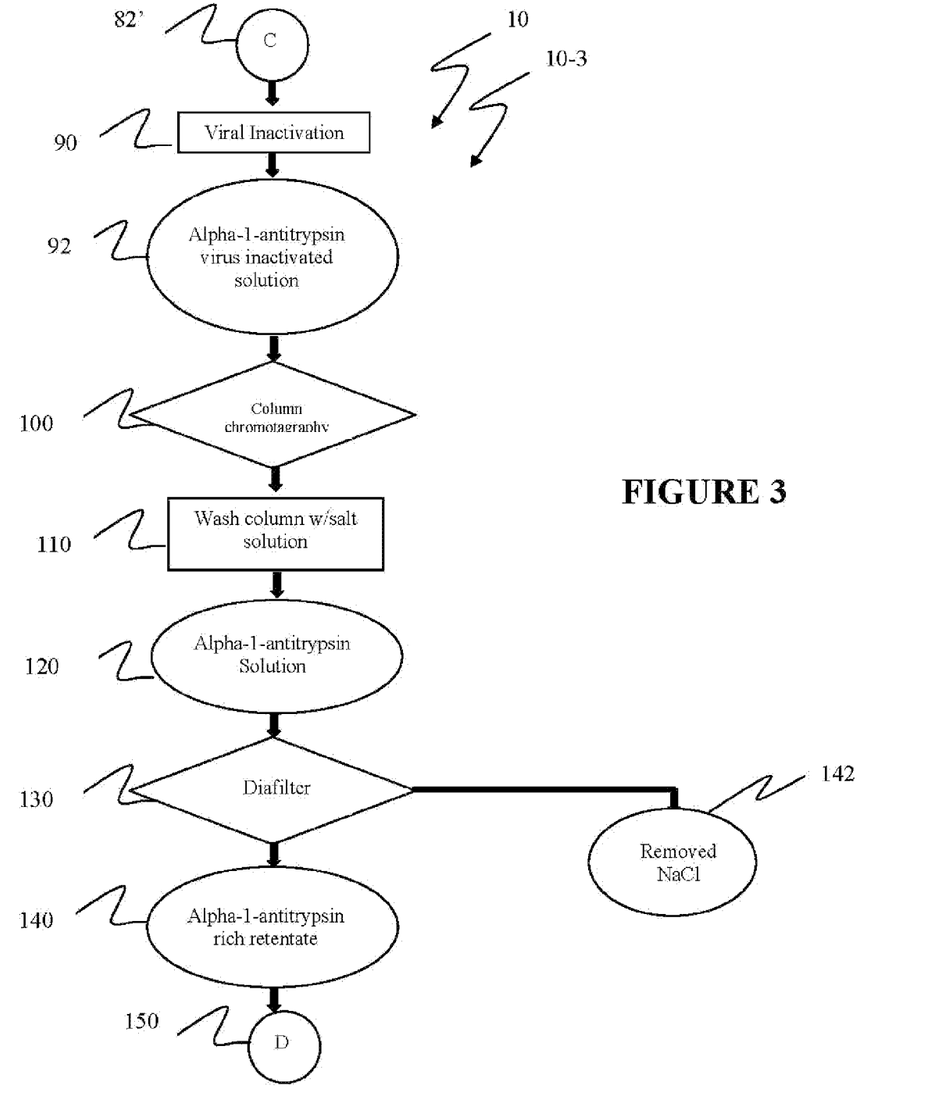
FIG. 3 is a flow diagram disclosing those procedural steps which immediately follow the steps seen in FIG. 2.

Reference is now made to FIG. 3 as point 82' for flow path portion 103 continues from point 82 of FIG. 2. Viral inactivation of the Alpha-1-antitrypsin product 80 may be accomplished as a double viral inactivation step involving a first solvent/detergent (S/D) method, followed by an augmented solvent/detergent (S/D) method. The first method employs raising the temperature of product 80 to approximately twenty-seven degrees Centigrade (temperature may range from twenty-four to thirty degrees Centigrade). A sufficient volume of TRITON X-100® or TWEEN-80® is then added to make a one percent solution and sufficient Tri-N-Butyl Phosphate to make a three tenths of one percent solution to make a first S/D added mixture. The first method continues by incubating the first S/D added mixture at twenty-seven degrees Centigrade for three hours during which time lipid enveloped viruses are inactivated. From this point, procedures currently available, inactivation and fractionation processes may be employed. However, a currently preferred process is hereafter provided for completeness.

For step 90, a S/D concentrate may be made as follows:

Add 30 milliliters of Tri-N-Butyl Phosphate to 800 milliliters of purified water. Mix well. Add 100 milliliters of either TRITON X-100® or TWEEN-80® to the mixed solution. Again, mix well to provide a final, mixed S/D solution. Add enough purified water to bring the total volume of the final mixed solution to 1000 milliliters. One more time, mix well. So made, the final solution is a 10× concentrate. Add 100 milliliters of this concentrate to each 900 milliliters of product 80 to form the first S/D added mixture.

After three hours of incubation, add, to the solution resulting from the first S/D method, sufficient formaldehyde to make a three tenths of one percent solution and sufficient phenol to make a three tenths of one percent solution to form an augmented mixture to begin the augmented method phase of step 90. Incubate at approximately twenty-seven degrees for an additional three hours, after which time non-enveloped and enveloped viruses are inactivated.

For step 90, an "augmented" concentrate may be made as follows:

Add 13.4 milliliters of thirty-seven and one-half percent formaldehyde solution to 900 milliliters of purified water. Mix well. Add fifty grams of phenol (reagent grade) to this mixture. Again, mix well. Add enough purified water to bring the total volume of the "augmented" preparation to one thousand milliliters. Once more, mix well. This preparations contains 50,000 parts per million each of formaldehyde and phenol (five percent of each). Measure the volume of the first S/D added mixture. Add 167 milliliters of augmented concentrate to each 833 milliliters of first S/D added mixture to form the augmented mixture.

Step 90 is completed by cooling the processed augmented mixture to a temperature of two to eight degrees Centigrade. So cooled, the augmented mixture becomes alpha-1-antitrypsin virus inactivated solution 92. Alternatively, viruses may be removed by other methods (e.g., chromatography, nanofiltration, pasteurization), if desired.

Step 100 involves use of column chromatography to remove viral inactivation chemicals, and is accomplished by the following sub-steps:

1. Set up a short, wide column with an appropriate ion exchange resin or specific alpha-1 anti-trypsin affinity resin known in the art that binds alpha-1-antitrypsin.
2. Introduce solution 92 into the exchange resin at a slow rate. Collect effluent liquid from the column and measure the effluent liquid in a high quality spectrophotometer. (As an example, a Beckman DU-7 with a deuterium light source may be used.) It should be noted that optical density of the effluent will increase as proteins are introduced into the resin column. Phenol in the viral inactivation solution (if used) also can increase measured optical density. After all of solution 92 has passed through the resin column and sterilants are washed from the column, begin collecting the effluent when measured optical density increases from its original value. A rise in optical density is indicative of protein in the effluent. After a period, optical density drops down to a level which is indicative of little or no protein in solution. At this point, collecting may cease. At this point, it is preferable to thoroughly wash the resin with deionized water. Bound material is alpha-1-antotrypsin. It is recommended that serum protein electrophoresis be performed to confirm that little or no alpha-1-antitrypsin has been released from the column.

Next in step 110 an appropriate concentration of sodium chloride solution is prepared to release the alpha-1-antitrypsin from the resin. As is well-known in the art, a sodium chloride solution is made by mixing and appropriate amount of NaCl (grams) into one liter of deionized water. Sufficient volume of the sodium chloride solution should be made to equal about ten times the volume of the resin column. The sodium chloride solution is then ran through the column, and the resulting alpha-1-antitrypsin solution 120 is collected.

Concurrently, the optical density of the effluent from the column is measured using a spectrophotometer with a one centimeter silica cuvette. Resultant optical density (OD) will be found to suddenly increase as alpha-1-antitrypsion is uncoupled from the resin and delivered into the effluent. Collect all high OD measured solution. When the OD of the effluent drops to a lower (normal) range, cease collecting the solution. The resulting solution is the alpha-1-antitrypsin solution 120. Note that a high OD is indicative of protein content in solution. In addition solution 120 contains sodium chloride which must be removed before any pure alpha-1-antitrypsin can be isolated.

Sodium chloride is preferably removed from solution 120 by a diafiltration step 130, employing a diafiltration system. Such may consist of a Millipore (or comparable) diafiltration system equipped with 30 KD cut-off membranes. The diafiltration solvent is purified water. The products of diafiltration are an alpha-1-antitrypsin rich retentate 140 and removed sodium chloride 142. It is recommended that serum electrophoresis be performed at this step in the process to confirm protein fractions in alpha-1-antitrypsin rich retentate.

Figure 4:
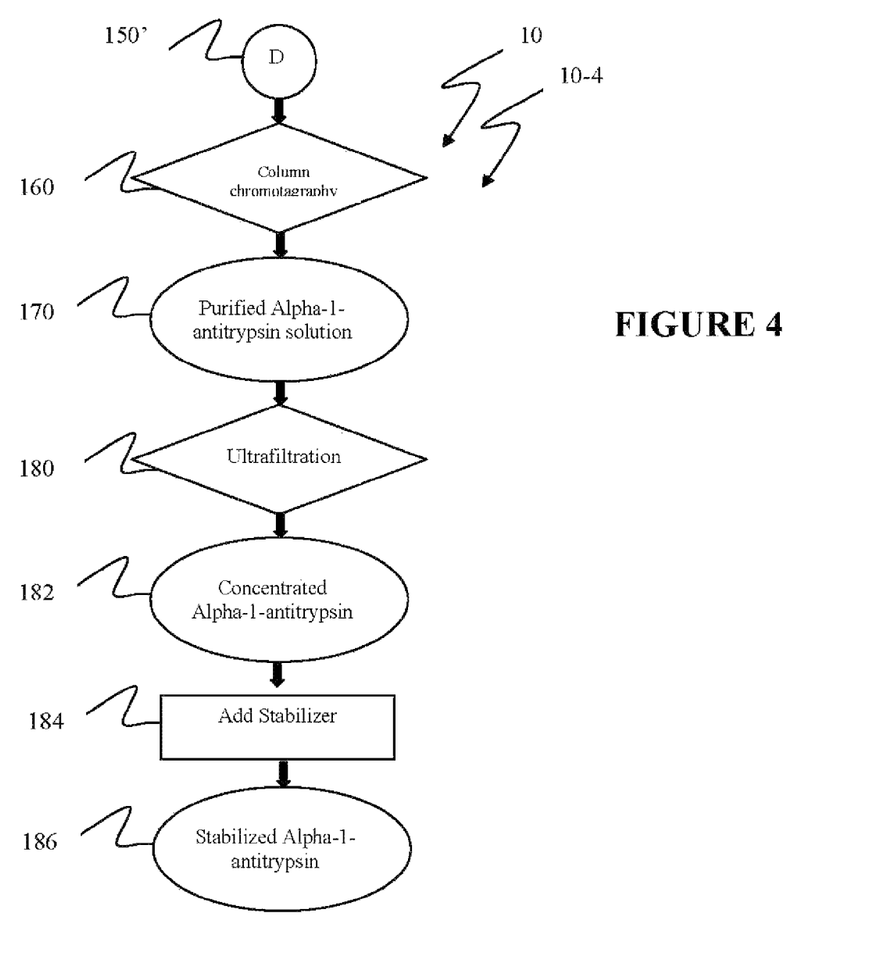
FIG. 4 is a flow diagram disclosing steps which immediately follow the steps seen in FIG. 3.

Reference is now made to FIG. 4 as point 150' for flow path portion 10-4 continues from point 150 of FIG. 3. In the final step 160 for purifying the alpha-1-antitrypsin rich retentate 140, it is preferred to set up a short, wide resin column with an appropriate ion exchange resin or specific alpha-1 antitrypsin affinity resin that allows alpha-1-antitrypsin to flow through the column. In this manner, any contaminating residual proteins are effectively separated to form a purified alpha-1-antitrypsin solution 170. The pooled solution is relatively dilute and is concentrated using step 180 via ultrafiltration. For such ultrafiltration, a hollow fiber filter may be used, or a Millipore ultrafiltration system (Pellicon) or equivalent, (10K to 30K dalton retentation) to concentrate the alpha-1-antitrypsin solution 182. Excess water is removed in the process of step 180. The resulting concentrate should have only a trace amount of sodium chloride and the pH should be approximately seven. In step 184, the alpha-1-antitrypsin concentrated solution 182 is stabilized by adding an appropriate amount of stabilizer known in the art, for example a maltose or sorbitol solution.

Optionally, to remove viruses from the stabilized alpha-1-antitrypsin solution 186, nanofiltration may be performed by passing solution 186 through a virus retaining membrane to produce a nanofiltered concentrate. Depending upon the execution of prior steps either stabilized alpha-1-antitrypsin concentrate 186 or optional nano-filtered alpha-1-antitrypsin concentrate is diluted with deionized water to produce a bulk purified alpha-1-antitrypsin solution. Contaminating bacteria may be removed from the bulk purified alpha-1-antitrypsin solution by passing the solution through a sterilizing filter to produce a sterilized bulk alpha-1-antitrypsin solution. Removed contaminating bacteria may be disposed of by methods currently known in the art. The resulting sterile solution may be filled into vials per standard procedures to produce a lot of vials. As required for quality assurance, final testing and inspection of the lot may be made.

Results of a Fractionation Procedure Performed According to the Instant Invention:

In order to show the efficacy and precision of separation of steps of the instant invention disclosed herein, the following results, using sodium citrate, have been extracted from a laboratory report, dated Aug. 8, 2005.

In the procedure, fresh frozen human plasma was used. As is typical in such procedures, a pool of cryo-poor plasma was made from four to eight bags of thawed plasma. Commercial equipment available from Beckman-Coulter was used to evaluate various fractions as they became available. A densitometer was used to scan the Beckman agarose gels for serum protein electrophoresis as part of a Paragon Electrophoresis System. For each fraction made from the pool, between three and five gel slits were loaded with five microliters of product. Results were averaged to obtain a better representative result for each fraction. Such results are found in tables provided hereafter.

The gels were electrophoresed for twenty-five minutes at 100 VDC at a pH of 8.6 and later stained with a Paragon blue stain. The densitometer was used to scan the stain-dried gels at a wavelength of 600 nanometers twice for each gel slit (ten gel slits per gel were used). An average graphic representation of the distribution of five different protein fractions, based upon density of attached dye as well as a numeric presentation of each fraction was derived. The numeric presentation was based upon a computer analysis of peaks and valleys of generated graphs at selected locations within the gel pattern as occurred between the anode and cathode on each gel. Presentation values were totaled and dye percentage was divided by the total dye amount to provide a percentage for evaluation. Note that the grand total, summing each individual blood fraction always equals one hundred percent.

As seen in Table II below, the five different protein fractions are identified as: Albumin, Alpha 1, Alpha 2, Beta and Gamma globulin. Before fractionation, a sample was removed from the pool and electrophoresed to determine the average fractional values of each fraction before beginning fractionation. Representative results for the average base pool material are listed below as percentages of whole plasma:

TABLE II

| Percentage content of each fraction | | | | | |
|---|---|---|---|---|---|
| | Albumin | Alpha 1 | Alpha 2 | Beta | Gamma |
| Base plasma | 61.2 | 7.1 | 9.7 | 13.0 | 8.9 |

Cryo-poor plasma from the pool was treated with the addition of a volume of fifty percent sodium citrate to a volume of plasma to make a twelve percent solution of sodium citrate. This mixture was stirred for sixty minutes at two to eight degrees Centigrade and was then centrifuged for sixty minutes at two to eight degrees Centigrade. The resulting supernatant solution 60 was measured. The remaining paste 62 was weighed and put into solution by addition of deionized water.

Supernatant 60 and paste 62 were dissolved and electrophoresed using procedures cited supra, the results of which are summarized in Table III, below:

TABLE III

| Resulting percentage concentrations | | | | | |
|---|---|---|---|---|---|
| | Albumin | Alpha 1 | Alpha 2 | Beta | Gamma |
| 12% Paste 62 (dissolved) | 67.8 | 2.7 | 9.1 | 20.4 | nd* |
| 12% Supernatant 60 | 28.6 | 1.5 | 10.7 | 40.3 | 16.1 |

*nd = none detected

There was no gamma globulin found in Paste 62 (dissolved). However, there was gamma globulin found in Supernatant 60.

Next, sufficient fifty percent solution sodium citrate was added to supernatant 60 to obtain a final mixture that contained twenty-two percent sodium citrate. This solution was also stirred for sixty minutes at two to eight degrees Centigrade: After centrifuging for sixty minutes at two to eight degrees Centigrade, the resulting supernatant solution 72 was measured. The remaining paste 70 was weighed and put into solution by the addition of deionized water (four times weight of paste 70 in milliliters) to form an IgG rich paste solution. Samples of supernatant 72 and IgG rich paste solution were electrophoresed by the procedure cited supra, the results of which are summarized in Table IV below:

TABLE IV

| Percentage concentrations of indicated solutions | | | | | |
|---|---|---|---|---|---|
| | Albumin | Alpha 1 | Alpha 2 | Beta | Gamma |
| 22% Supernatant 72 | 82.4 | 13.9 | 3.6 | nd* | nd* |
| 22% Sol. 100 (dissolved) | 16.7 | 1.3 | 10.5 | 32.5 | 39.0 |

*nd = none detected

There was no gamma globulin found in supernatant 72. However, there was gamma globulin found in IgG rich solution To remove sodium citrate trapped in the twenty-two percent paste solution, a Pellicon unit was selected to diafilter the IgG rich paste solution. On the average, about seven times the volume of the IgG rich paste solution was required to diafilter the sodium citrate and bring conductivity of the resulting solution down to a range between 400 and 800 microSiemens/centimeter (μS/cm), before performing any column work.

At this point, various currently employed methods could have been used to purify the gamma globulin and alpha-1-antitrypsin. In the case of this experiment, the solution was first treated with a Solvent/Detergent solution of three hours at twenty-seven degrees Centigrade. Then an augmented sterilization solution, performed according to U.S. Pat. No. 6,881,573, titled AUGMENTED SOLVENT/DETERGENT METHOD FOR INACTIVATING ENVELOPED AND NON-ENVELOPED VIRUSES, issued to Allan L. Louderback, filed Sep. 12, 2003, was added to the mixture and further incubated for an additional three hours at twenty-seven degrees Centigrade. This dual inactivation treatment of the dialyzed diafiltered solution inactivates both enveloped and non-enveloped viruses.

The sterile treated solution was transferred to an ion exchange column loaded with TOYOPEARL® CM-650C resin. The resin adsorbed gamma globulin and allowed all of the other proteins present in solution to flow out in effluent from the column. After adding the solution to the column and adjusting the column flow to slowly drip out through the effluent end, effluent solution was measured at 280 nanometers to determine when all free proteins and sterilants had been transported through the column. Afterward, the column was washed with a two times volume of purified water to assure that the effluent has a very low measured optical density at 280 nanometers.

A two percent solution of sodium chloride was then dispensed onto the top of the column and allowed to percolate through the column. Gamma globulin which was adsorbed by resin particles was freed to flow out of the column into a receiving vessel.

Collected effluent from the column with purified water (labeled as Purified Water) and effluent from the column with the two percent solution (labeled as two percent NaCl) were tested electrophoretically to show the result of selected isolation and release of gamma globulin from the resin particles. Results of this step is summarized in Table VI, seen below:

TABLE VI

Resulting percentage fractions

| | Albumin | Alpha 1 | Alpha 2 | Beta | IgG |
|---|---|---|---|---|---|
| Purified Water | 26.0 | 2.7 | 15.2 | 57.0 | nd* |
| Two Pecent NaCl | nd* | nd* | nd* | 1.9 | 98.1 |

*nd = none detected

Note that more than 98% of the gamma globulin was isolated in the first resin treatment. The value for beta globulin of 1.9% may be the result of an application spot when applying solution to gel. The two percent sodium chloride solution contained the gamma globulin (IgG) and, perhaps, with larger pools of plasma, may contain some IgA and IgM globulins which should be removed.

The two percent sodium chloride solution was therefore diafiltered to remove the sodium chloride for a next column treatment. Diafiltration was again performed by passing the solution though a Pellicon unit whereby the salt was removed, yielding a product which had a conductivity of 400 to 800 microSeimens/centimeter (µS/cm). Note that it likely takes about six volumes of deionized purified water to diafilter the two percent solution.

As a final step, a column was filled with TOYOPEARL® 560-C resin and the desalted solution was added to the top of the column and allowed to slowly percolate through the column. In this column, IgG flowed right through the resin and all other proteins attached to the resin (e.g., IgA and IgM) to yield a final effluent from the column that was 100% IgG in an aqueous base. The effluent tested is seen in Table VII below:

TABLE VII

Percentage content of final solution

| | Albumin | Alpha 1 | Alpha 2 | Beta | IgG |
|---|---|---|---|---|---|
| Solution 172 | nd* | nd* | nd* | nd* | 100 |

*nd = none detected

Other experiments have been performed using various salts in fractionating fresh frozen plasma. Steps 52, 54 and 64 were repeated using the various salts to complete the fractionation procedure in the two stages as outlined supra. As seen in Table VIII, below, and consistent with the method disclosed for sodium citrate, the first fractionation comprised mixing a set volume of plasma with a first predetermined volume of concentrated salt solution, where possible. Where it was not possible to achieve a necessary concentration of salt by dissolving salt in water, dry salts were simply added to achieve the desired concentration, by weight.

The first predetermined volume of salt solution was twelve percent by weight. Reaction mixing followed at two to eight degrees Centigrade for one hour. After reaction mixing, the resulting mixture was spun down at two to eight degrees Centigrade at 4500 rpm for one hour. A first supernatant fluid 60 overlying a paste precipitant 62 was gently poured off and collected. Note that the first supernatant fluid 60 contained a twelve percent solution, by weight, of the salt used. Generally, the resulting paste precipitant 62 was diluted with a percentage by weight of deionized water (usually four times the weight of collected paste 62) and stored at two to eight degrees overnight for further analysis.

Per step 64, volume of supernatant 60 was measured and an amount of concentrated salt solution was added to raise the concentration of salt to a level of twenty-two percent, by weight. The resulting composition was mixed for one hour at two to eight degrees Centigrade and then refrigerated overnight. The following morning, the composition was mixed again briefly for about five minutes and then centrifuged for one hour at 4500 rpm at two to eight degrees Centigrade. Any supernatant, supernatant 72, was poured off and saved for any desired further processing. Paste 70, the target of this procedure, after separation from supernatant 72, was weighed and diluted (redissolved per step by adding an amount of deionized water calculated to be about four times the weight of paste 70).

The above disclosed procedure was repeated for both organic and inorganic salts in various combinations. Table VIII, shown below, provides results of the procedure as determined by serum electrophoresis performed using the Beckman-Coulter system, Results of the electrophoresis were scanned with the Beckman-Coulter scanner and are presented as the percentage of protein at each of five levels, name as albumin, alpha-1, alpha-2, beta and IgG. The total for each scan, by the Beckman algorithm, approximates 100% when summed

TABLE VIII

Serum Electrophoresis Results of Salt Fractionations - showing % of each fraction

| Expt. Num | Stage 1 12% | Stage 2 22% | Albumin | Alpha1 | Alpha2 | Beta | IgG |
|---|---|---|---|---|---|---|---|
| 1 | Ammonium sulfate | Ammonium sulfate | 18.1 | 1.9 | 25.6 | 24.6 | 29.9 |
| 2 | Sodium citrate | Sodium citrate | 19.4 | 1.4 | 10.1 | 35.4 | 33.2 |
| 3 | Ammonium sulfate | Sodium citrate | 17.0 | 1.6 | 9.6 | 26.4 | 45.5 |
| 4 | Sodium Citrate | Ammonium sulfate | 17.9 | 1.6 | 12.6 | 24.7 | 43.2 |

There was no IgG found in the paste 62 nor in the supernatant 72. All of the IgG is found in paste 70. One should not be confused because values are higher for IgG for mixed organic (sodium citrate) and inorganic (ammonium sulfate) salts. Such is a result of a differential extraction of other proteins from the plasma. Some proteins have different precipitation patterns with different salts.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of extracting alpha-1-antitrypsin from plasma, comprising:
    providing a non-salted, non-precipitated, previously frozen blood product;
    salting the previously frozen blood product to produce a first intermediate having a total salt content of between 11-13% wt;
    centrifuging the first intermediate to produce a first supernatant and a first paste;
    salting the first supernatant to produce a second intermediate with a total salt content of between at least 21-23% wt;
    centrifuging the second intermediate to produce a second supernatant and a second paste;
    rehydrating the first paste, de-salting the first paste and the second supernatant, and passing the de-salted first paste and second supernatant through at least one of an ion exchange column or an affinity column to produce a first and second alpha-1-antitrypsin effluent; and
    combining the first and second effluents to produce a product containing the alpha-1-antitrypsin.

2. The method of claim 1, wherein the step of salting the previously frozen blood product comprises adding an amount of a first salt selected from the group consisting of a citrate, an acetate, and a gluconate.

3. The method of claim 2, wherein the first salt is selected from the group consisting of a sulfate and a chloride.

4. The method of claim 2, wherein the citrate comprises a sodium citrate solution.

5. The method of claim 1, wherein the first intermediate has a total salt content of 12% wt.

6. The method of claim 1, wherein the step of salting the first supernatant comprises adding an amount of a second salt selected from the group consisting of a citrate, an acetate, and a gluconate.

7. The method of claim 6, wherein the second salt is selected from the group consisting of a sulfate and a chloride.

8. The method of claim 6, wherein the citrate comprises a sodium citrate solution.

9. The method of claim 1, wherein the second intermediate has a total salt content of 22% wt.

10. The method of claim 1, further comprising processing the first paste and the second supernatant to recover a quantity of albumin.

11. The method of claim 1, further comprising processing the second paste to recover a quantity of IgG.

12. The method of claim 1, wherein the step of rehydrating the first paste comprises adding water to the first paste.

13. The method of claim 1, wherein the step of de-salting the first paste and the second supernatant comprises using a diafiltration membrane.

14. The method of claim 1, wherein the previously frozen blood product comprises a cryo-poor plasma.

* * * * *